US010801034B2

(12) United States Patent
Pereira et al.

(10) Patent No.: US 10,801,034 B2
(45) Date of Patent: Oct. 13, 2020

(54) METHODS OF INCREASING RESISTANCE OF CROP PLANTS TO HEAT STRESS AND SELECTING CROP PLANTS WITH INCREASED RESISTANCE TO HEAT STRESS

(71) Applicant: THE BOARD OF TRUSTEES OF THE UNIVERSITY OF ARKANSAS, Little Rock, AR (US)

(72) Inventors: Andy Pereira, Fayetteville, AR (US); Ramegowda Venkategowda, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 15/967,021

(22) Filed: Apr. 30, 2018

(65) Prior Publication Data

US 2018/0320193 A1 Nov. 8, 2018

Related U.S. Application Data

(63) Continuation of application No. 14/776,329, filed as application No. PCT/US2014/025923 on Mar. 13, 2014, now Pat. No. 9,957,520.

(60) Provisional application No. 61/779,124, filed on Mar. 13, 2013.

(51) Int. Cl.
| | |
|---|---|
| *C12N 15/82* | (2006.01) |
| *C07K 14/415* | (2006.01) |
| *C12Q 1/68* | (2018.01) |
| *C12Q 1/6895* | (2018.01) |

(52) U.S. Cl.
CPC ........ *C12N 15/8261* (2013.01); *C07K 14/415* (2013.01); *C12N 15/8271* (2013.01); *C12Q 1/6895* (2013.01); *C12Q 2600/13* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 7,511,190 B2 | 3/2009 | Creelman et al. | |
| 9,957,920 B2 * | 5/2018 | Walser | F02M 21/0233 |
| 2002/0102695 A1 | 8/2002 | Silva et al. | |
| 2003/0236208 A1 | 12/2003 | Kmiec et al. | |
| 2004/0123343 A1 | 6/2004 | La Rosa et al. | |
| 2006/0059590 A1 | 3/2006 | Cerny et al. | |
| 2007/0192889 A1 | 8/2007 | La Rosa et al. | |
| 2008/0263722 A1 | 10/2008 | Hu et al. | |
| 2009/0300790 A1 | 12/2009 | Aharoni et al. | |
| 2010/0162432 A1 * | 6/2010 | Puzio | C12N 15/8271 800/276 |
| 2014/0223604 A1 | 8/2014 | Pereira et al. | |

FOREIGN PATENT DOCUMENTS

| | | |
|---|---|---|
| WO | 2007030001 | 3/2007 |
| WO | 2008142036 | 11/2008 |
| WO | 2012158594 | 11/2012 |

OTHER PUBLICATIONS

Whisstock J.C. et al. Prediction of protein function from protein sequence and structure. Q Rev Biophys. Aug. 2003;36(3):307-40. Review. (Year: 2003).*
Rhoads D.M. et al. Regulation of the cyanide-resistant alternative oxidase of plant mitochondria. Identification of the cysteine residue involved in alpha-keto acid stimulation and intersubunit disulfide bond formation. J Biol Chem. Nov. 13, 1998;273(46):30750-6. (Year: 1998).*
Sjolander. Phylogenomic inference of protein molecular function: advances and challenges. Bioinformatics. Jan. 22, 2004;20(2):170-9. (Year: 2004).*
Zhang et al. Comparative proteomic study reveals dynamic proteome changes between superhybrid rice LYP9 and its parents at different developmental stages. Journal of Plant Physiology. Mar. 1, 2012;169(4):387-98. Epub Dec. 29, 2011. (Year: 2012).*
International Application No. PCT/US2012/037730, International Preliminary Report on Patentability, dated Nov. 28, 2013, 8 pages.
International Application No. PCT/US2012/037730, International Search Report and Written Opinion, dated Nov. 30, 2012, 15 pages.
Jeong, J. S. et al., "Root-Specific expression of OsNAC10 improves drought tolerance and grain yield in rice under field drought conditions," (2010) Plant Physiology 153:185-197.
Oh, S-J, et al., "Overexpression of the transcription factor AP37 in rice improves grain yield under drought conditions," (2009) Plant Physiology 150:1368-1379.
Puzio, P. et al., NCBI GenBank: GM965114.1, Sequence 446 from WO2008142036, Dec. 17, 2008, 1 page.
Office Action dated Nov. 30, 2015 for U.S. Appl. No. 14/117,422, 41 pages.
Rogers, R. L. et al., "Formation and longevity of chimeric and duplicate genes in *Drosophila melanogaster*," (2009) Genetics 181:313-322.
Chimeric Gene, Wikipedia definition, https://en.wikipedia.org/wiki/Chimeric gene, Nov. 16, 2015.
Keskin, O. et al., "A new, structurally nonredundant, diverse data set of protein—protein interfaces and its implications," (2004) Protein Science 13:1043-1055.

(Continued)

*Primary Examiner* — Cynthia E Collins
(74) *Attorney, Agent, or Firm* — Quarles & Brady LLP

(57) ABSTRACT

Methods of increasing the resistance of a crop plant to heat stress and in particular methods of improving the grain yield and quality of crop plants grown under heat stress in the form of increased minimal temperatures are provided. The methods include selecting plants with increased expression of HYR and growing these plants in regions expected to experience minimal temperatures above 25° C. during the growing season. Methods of screening plants for increased resistance to heat stress and methods of producing grain in regions having minimal temperatures of 25° C. or more are also provided.

10 Claims, 2 Drawing Sheets

Specification includes a Sequence Listing.

(56) References Cited

OTHER PUBLICATIONS

Guo, H. H. et al., "Protein tolerance to random amino acid change," (2004) PNAS 101:9205-9210.
Thornton, J.M. et al., "From structure to function: approaches and limitations," Nat Struct Biol., Supp Nov. 2000:991-994.
Nakano, T. et al., "Genome-wide analysis of the ERF gene family in arabidopsis and rice," (2006) Plant Physiology 140:411-432.
Rashid, M. et al., "AP2/ERF transcription factor in rice: Genome-wide canvas and syntenic relationships between monocots and eudicots," (2012) Evolutionary Bioinformatics 8:321-355.
Ambavaram, M. M. R. et al., "Coordinated regulation of photosynthesis in rice increases yield and tolerance to environmental stress," (2014) Nature Communications 5:5302 (14 pages).
Batlang, U., "Identification of drought-responsive genes and validation for drought resistance in rice," (2010) Dissertation submitted to the faculty of Virginia Polytechnic Institute and State University, Jan. 5, 2010. Retrieved from the Internet: <URL: http://scholar.lib.vt.edu/theses/available/etd-01212010-141508/> on Jun. 10, 2014.
Huang, et al., "Identification and characterization of proteins associated with plant tolerance to heat stress," (2008) Journal of Integrative Plant Biology, 50:1230-1237.
Usui, et al., "Heat-tolerant rice cultivars retain grain appearance quality under free-air CO2 enrichment," (2014) Rice 7:1-9.
International Application No. PCT/US2014/025923, International Search Report and Written Opinion, dated Jul. 8, 2014 (16 pages).
International Application No. PCT/US2014/025923, International Preliminary Report on Patentability, dated Sep. 24, 2015 (9 pages).
Zhang, C. et al., "Comparative proteomic study reveals dynamic proteome changes between superhybrid rice LYP9 and parents at different developmental stages," Journal of Plant Physiology (2012) 169:387-398.
Office Action dated Mar. 21, 2017 for U.S. Appl. No. 14/776,329.

\* cited by examiner

SEQUENCE LISTING

```
<160> NUMBER OF SEQ ID NOS: 4

<210> SEQ ID NO 1
<211> LENGTH: 200
<212> TYPE: PRT
<213> ORGANISM: Oryza sativa subsp. japonica cultivar Nipponbare
<220> FEATURE:
<221> NAME/KEY: misc_feature
<223> OTHER INFORMATION: Sequence of HYR protein, Os03g0117900 protein

<400> SEQUENCE: 1

Met Asp Arg Asp Glu Ser Leu Gly Thr Gln Pro Leu Thr Gly Arg Arg
1               5                   10                  15

Val Arg Ala Asp Thr Arg His Pro Val Tyr Arg Gly Ile Arg Leu Arg
            20                  25                  30

Ser Gly Lys Trp Val Ser Glu Ile Arg Glu Pro Gly Lys Ser Ser Arg
        35                  40                  45

Ile Trp Leu Gly Thr Tyr Pro Thr Pro Glu Met Ala Ala Ala Ala Tyr
    50                  55                  60

Asp Ala Ala Ala Leu Ala Leu Arg Gly Ala Asp Ala Ala Leu Asn Phe
65                  70                  75                  80

Pro Gly Thr Ala Thr Ser Arg Pro Ala Pro Ala Ser Gly Ser Pro Asp
                85                  90                  95

Asp Ile Arg Ala Ala Ala Ala Ala Ala Ala Met Ile Gly Ser Gly
            100                 105                 110

His Arg Gly Asn Gln Arg Ala Ala Asp Ala Ser Thr Ser Arg Ala Ala
        115                 120                 125

Thr Ala Ala Pro Glu Ala Ala Val Ala Ala Gly Ala Gly Asp Gln Lys
    130                 135                 140

Arg Val Val Asp Glu Asp Asp Val Phe Glu Met Pro Arg Leu Leu Val
145                 150                 155                 160

Ser Met Ala Glu Gly Leu Met Met Ser Pro Pro Arg Leu Ser Pro Ser
                165                 170                 175
```

Thr Asp Gly Val Gly Gly Val Ser Pro Glu Asp Asp Glu Glu Asp
                180                 185                 190

Gly Met Ser Leu Trp Asn His Ser
        195                 200

<210> SEQ ID NO 2
<211> LENGTH: 603
<212> TYPE: DNA
<213> ORGANISM: Oryza sativa subsp. japonica cultivar Nipponbare
<220> FEATURE:
<221> NAME/KEY: misc_feature
<223> OTHER INFORMATION: DNA sequence of rice HYR gene, Gene
      Os03g0117900

<400> SEQUENCE: 2
atggatcgag acgagagctt gggcacgcag ccattgaccg ggaggcgggt gcgcgcggac      60
acaaggcacc cggtgtaccg cggcatccgg ctccgcagcg gcaagtgggt ctcggagatc     120
cgcgagccgg gcaagtccag caggatctgg ctcggcacgt acccgacgcc cgagatggcc     180
gccgcggcgt acgacgccgc ggcattggcg ctgcgcggcg ccgacgccgc gctcaacttc     240
cccggcacgg ccacgtcgcg cccggcgcca gcctccggct ccccgacga catccgcgca      300 gcggccgcgg ccgccgccgc gatgatcggc tccggtcacc gtggcaacca gcgcgccgcc     360
gacgcgagca cgtctcgcgc ggcgacggcg gcgccggagg ccgccgtcgc cgctggggcg     420
ggcgatcaga agcgcgtcgt ggacgaggac gacgtcttcg agatgccgcg gctgctggtg     480
agcatggccg agggcttgat gatgagcccg ccgaggctga gccctcgac ggacggcgtc      540 ggcggcgtgt cgccggagga cgacgaggac gaggacggca tgagcctgtg gaaccattcc     600
tga                                                                   603

<210> SEQ ID NO 3
<211> LENGTH: 199
<212> TYPE: PRT
<213> ORGANISM: Oryza sativa subspecies Indica
<220> FEATURE:
<221> NAME/KEY: misc_feature
<223> OTHER INFORMATION: Rice Indica HYR gene, Locus OsI_09748

<400> SEQUENCE: 3

Met Asp Arg Asp Glu Ser Leu Gly Thr Gln Pro Leu Thr Gly Arg Arg
1               5                   10                  15

Val Arg Ala Asp Thr Arg His Pro Val Tyr Arg Gly Ile Arg Leu Arg
            20                  25                  30

Ser Gly Lys Trp Val Ser Glu Ile Arg Glu Pro Gly Lys Ser Ser Arg
        35                  40                  45

Ile Trp Leu Gly Thr Tyr Pro Thr Pro Glu Met Ala Ala Ala Ala Tyr
    50                  55                  60

Asp Ala Ala Leu Ala Leu Arg Gly Ala Asp Ala Ala Leu Asn Phe
65                  70                  75                  80

Pro Gly Thr Ala Thr Ser Arg Pro Ala Pro Ala Ser Gly Ser Pro Asp
                85                  90                  95

Asp Ile Arg Ala Ala Ala Ala Ala Ala Ala Met Ile Gly Ser Gly
            100                 105                 110

His Arg Gly Asn Gln Arg Ala Ala Asp Ala Ser Thr Ser Arg Ala Ala
        115                 120                 125

Pro Ala Pro Glu Val Ala Val Ala Ala Gly Ala Gly Asp Gln Lys Arg
    130                 135                 140

```
Val Val Asp Glu Asp Asp Val Phe Glu Met Pro Arg Leu Leu Val Ser
145                 150                 155                 160

Met Ala Glu Gly Leu Met Met Asn Pro Pro Arg Leu Ser Pro Ser Thr
                165                 170                 175

Asp Gly Val Gly Gly Val Ser Pro Glu Asp Asp Glu Asp Glu Asp Gly
            180                 185                 190

Met Ser Leu Trp Asn His Ser
        195

<210> SEQ ID NO 4
<211> LENGTH: 257
<212> TYPE: PRT
<213> ORGANISM: Sorghum bicolor
<220> FEATURE:
<221> NAME/KEY: misc_feature
<223> OTHER INFORMATION: SORBIDRAFT_01g049400 Protein sequence

<400> SEQUENCE: 4

Met Ala Val Ala Val Ala Val Val Ser Gly Thr Gly Ile Ala His Leu
1               5                   10                  15

His Phe Leu His Val Leu Leu Pro Glu Ile Pro Gly Phe Ser Gly Glu
                20                  25                  30

Glu Gln Arg Gly Ser Val Pro Val Cys Pro Glu Cys Pro Gly Gln Met
            35                  40                  45

Glu Arg Glu Gln Glu Gln Glu Ala Gly Thr Ala Gln Gln Leu Leu Gly
50                  55                  60

Arg Arg Val Arg Ala Asp Thr Arg His Pro Val Tyr Arg Gly Ile Arg
65                  70                  75                  80

Tyr Arg Gly Gly Lys Trp Val Ser Glu Ile Arg Glu Pro Arg Lys Ser
                85                  90                  95

Asn Arg Ile Trp Leu Gly Thr Tyr Pro Ala Pro Glu Met Ala Ala Ala
            100                 105                 110

Ala Tyr Asp Ala Ala Ala Leu Ala Leu Arg Gly Ala Glu Ala Ala Leu
        115                 120                 125

Asn Phe Pro Gly Ala Ala Met Ser Arg Pro Ala Pro Ala Ser Cys Ser
    130                 135                 140

Pro Asp Asp Ile Arg Ala Ala Ala Ala Ala Ala Ala Ala Ala Val Ile
145                 150                 155                 160

Gly Arg Ser His Ser Pro Gln Val Gly Gly Glu Ala Ala Ala Gly Gly
                165                 170                 175

Gly Cys Gly Ala Ser Thr Trp Ser Ser Gly Ala Gly Ala Gln Gly Gln
            180                 185                 190

Val Pro Glu His Arg Ala Gly Asp Arg Arg Ile Val Asp Glu Asp Asp
        195                 200                 205

Val Phe Gln Val Pro Arg Leu Leu Ala Gly Met Ala Glu Gly Leu Met
    210                 215                 220

Met Ser Pro Pro Arg Leu Val Gly Pro Ala Thr Asp Gly Ala Val Leu
225                 230                 235                 240

Leu Glu Glu Asp Gly Ser Glu Asp Gly Val Val Ser Leu Trp Asp His
                245                 250                 255

Ser
```

METHODS OF INCREASING RESISTANCE OF CROP PLANTS TO HEAT STRESS AND SELECTING CROP PLANTS WITH INCREASED RESISTANCE TO HEAT STRESS

CROSS-REFERENCE TO RELATED APPLICATIONS

This patent application is a divisional application of U.S. patent application Ser. No. 14/776,329, filed on Sep. 14, 2015, issued May 1, 2018 as U.S. Pat. No. 9,957,520, which is a national stage filing under 35 U.S.C. 371 of International Application No. PCT/US2014/025923, filed Mar. 13, 2014, which claims the benefit of priority of U.S. Provisional Patent Application No. 61/779,124, filed Mar. 13, 2013, both of which are incorporated herein by reference in their entirety.

STATEMENT REGARDING FEDERALLY SPONSORED RESEARCH

This invention was made with United States government support awarded by the United States Department of Agriculture grant number 2009-35900-05968 and National Science Foundation grant number DBI-0922747. The United States has certain rights in this invention.

SEQUENCE LISTING

This application is being filed electronically and includes an electronically submitted Sequence Listing in .txt format. The .txt file contains a sequence listing entitled "2014-03-13 5658-00204_ST25.txt" created on Mar. 12, 2014 and is 7.34 kilobytes in size. The Sequence Listing contained in this .txt file is part of the specification and is hereby incorporated by reference herein in its entirety.

INTRODUCTION

This invention relates to methods of increasing the resistance to heat stress in plants and methods of screening for additional sequences involved in increasing resistance to heat stress.

Increased temperature has been recognized as a factor reducing yield in rice, with varying effects on the three growth stages: a) vegetative—in establishment of panicle initiation; b) reproductive—panicle initiation to flowering; c) ripening—flowering to grain maturation (Welch 2010). Rice grain yield can be affected by high temperatures through two mechanisms: i) high maximum temperatures in combination with high humidity can cause spikelet sterility and reduced grain quality, and (ii) increased nighttime temperatures that may reduce assimilate accumulation (Wassman et al., 2009).

Climate change has caused an increase in daytime and nighttime temperatures that can cause stress on plants. Means of identifying plants with increased resistance to heat stress and the ability to grow and produce high grain yields of good quality grain are needed to deal with the expected increased temperatures in arable areas to ensure the food supply are needed.

SUMMARY

Methods of increasing the resistance of crop plants to heat stress are provided herein. The methods include selecting crop plants for increased expression of the HYR protein of SEQ ID NO: 1, 3, 4, an ortholog thereof, or a sequence with at least 80% identity to SEQ ID NOs: 1, 3, or 4 as compared to a control. The increased expression of the HYR protein correlates with increased resistance to heat stress and provides for improved grain quality or improved grain yield of the crop plants in particular when the plants are grown under conditions or in regions where the minimal temperature is 25° C. or above.

In another aspect, the methods of screening for crop plant proteins capable of increasing resistance of crop plants to heat stress are provided. First the sequences whose expression is increased or decreased in response to expression of a HYR protein are identified. The HYR protein has a polypeptide sequence selected from those of SEQ ID NO: 1, SEQ ID NO: 3, SEQ ID NO: 4, an ortholog of these sequences or a sequence with at least 80% identity to at least one of SEQ ID NOs: 1, 3, or 4. Then the sequences are analyzed to determine if they are required for resistance to heat stress in a plant cell or transgenic plant. Those sequences that are required for resistance to heat stress may be useful targets for generation of plants with increased resistance to heat stress.

In a further aspect, methods of using an HYR protein to investigate resistance to heat stress in plants are provided. The methods include generating a transgenic plant comprising a polynucleotide sequence encoding the HYR protein operably connected to a promoter or transcription regulatory sequence active in plant cells and capable of increasing the expression of the HYR protein in the transgenic plant relative to a control plant, and growing the transgenic plant in conditions of heat stress in which the minimal night temperature is 25° C. or above. The transgenic plants may then be used to analyze and identify other sequences required for optimal heat stress response in crop plants.

In a still further aspect, a method of producing grain in regions having minimal temperatures of 25° C. or above are provided. These methods include selecting a crop plant having at least two fold increased expression of the HYR protein as compared to a control plant and planting this crop plant in a region expected to or at risk of having minimal temperatures of 25° C. or above during the growing season of the plant. These plants are expected to yield increased grain on a per plant or per planting area basis and the quality of the grain is expected to be high with reduced chalkiness as compared to control plants.

DETAILED DESCRIPTION

Figure 1:
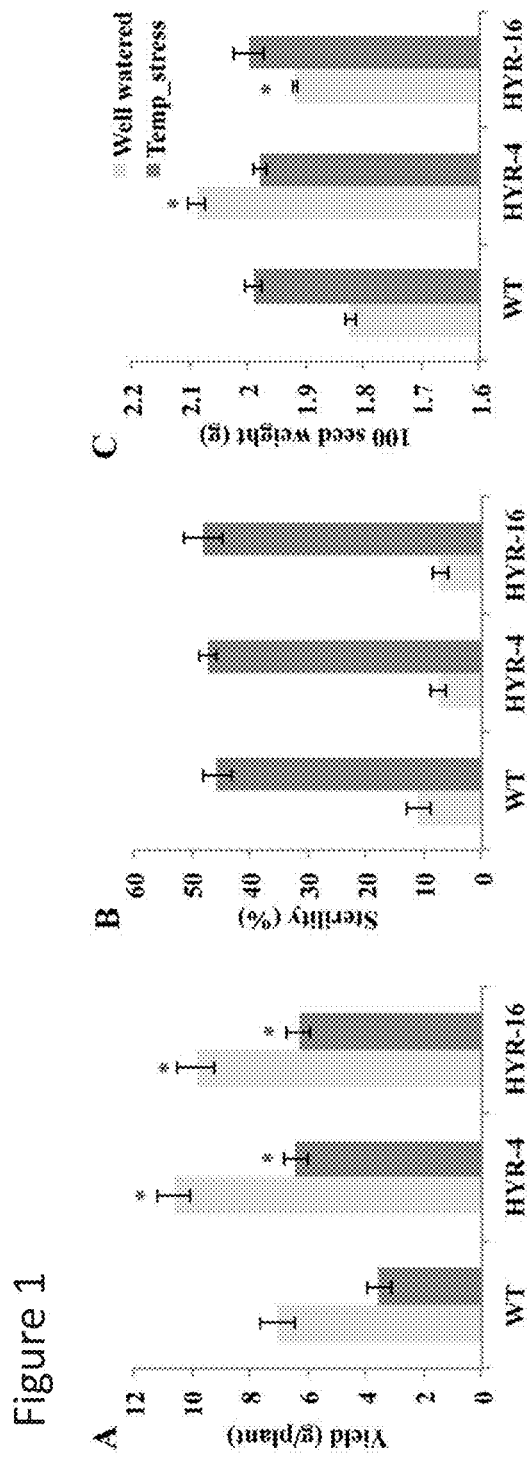
FIG. 1 is a set of graphs showing the temperature stress response of rice HYR overexpression lines as compared to controls. The effect of temperature stress on A) Yield; B) Spikelet sterility; and C) Seed weight is shown. Plants at early boot stage were exposed to high day/night temperature of 36/26° C. until physiological maturity (Temp. stress) compared to plants under ambient conditions of 28/20° C. (well-watered). Values are the mean±SE (n>6) and '*' indicates significant difference from wild-type, t-test at P≤0.05.

Environmental stresses such as drought, heat, cold and salinity affect the survival and growth of plants. Plants can respond to such stresses by a change in expression of genes and physiological processes to tolerate or adapt to the stresses. Transcription factors regulate the expression of genes involved in normal growth and development as well as response to environmental signals. Plants experiencing environmental stresses such as drought, cold and heat, respond quickly by altering the expression of transcription factors and other regulatory genes that can coordinately regulate the response of the plant. Stress responsive transcription factors regulate cascades of gene expression that can help a plant adapt to or tolerate the environmental stress factors (Qin et al., 2011). Transcription factors have therefore been used in overexpression studies in model and crop plants to generate plants that are resistant to specific or multiple stresses.

As noted above, increased temperature has been recognized as a factor reducing yield in rice, with varying effects on the three growth stages: a) vegetative—in establishment of panicle initiation; b) reproductive—panicle initiation to flowering; c) ripening—flowering to grain maturation (Welch 2010). Rice grain yield can be affected by high temperatures through two mechanisms: i) high maximum temperatures in combination with high humidity can cause spikelet sterility and reduced grain quality, and (ii) increased nighttime temperatures that may reduce assimilate accumulation (Wasseman et al., 2009).

Climate change has caused an increase in daytime and nighttime temperatures that can cause stress on plants. To quantify this effect, temperature data at IRRI was analyzed for the period 1979-2003 (Peng et al., 2004) and showed that annual mean maximum and minimum temperatures increased by 0.35 and 1.13° C., respectively, revealing a close correlation between rice grain yield and mean minimum (nighttime) temperature. Grain yield declined by 10% for each 1° C. increase in minimum temperature, with the effect of maximum temperature being insignificant. More recently an analysis of intensely managed irrigated rice fields (Welch et al., 2010) showed that temperature affected both the vegetative and ripening phases of the rice crop, with higher minimum temperature reducing yield, and higher maximum temperature raising it.

The vegetative growth stage in rice can tolerate high temperatures to about 35/25° C. day/night regime, with temperatures higher than this critical level reducing plant height, tiller number, total dry weight and yield potential (Yoshida et al., 1981). Photosynthesis was shown to be reduced by 11.2% and 35.6% at temperatures of 3.6° C. and 7.0° C. higher than ambient during heading to middle ripening stage (Ohe et al., 2007). The effect on photosynthesis was shown to be by affecting thylakoid organization, stacking of grana in the chloroplast or its ability to swell (Wahid et al., 2007). High temperature can loosen the bonds between membranes of the photosynthetic organelles leading to an increase in fluidity of lipid layer (Savchenko et al., 2002) and increased solute leakage. Thus electrolyte leakage or cellular membrane thermostability can be used as a measure of heat tolerance in crops (Prasad et al., 2006; Tripathy et al., 2000).

Reproductive stage in rice is more heat sensitive than the vegetative stage (Yoshida et al., 1981), with anthesis as the most sensitive process followed by microgametogenesis. High temperature of >35° C. can reduce pollen viability and cause spikelet sterility (Matsui et al 2000). The meiotic stages during tetrad formation and young microspore formation are most sensitive to high temperature during microsporogenesis (Yoshida et al., 1981), as well as drought (Sheoran and Saini, 1996) and cold stress (Imin et al., 2004).

Heat stress during anthesis leads to an irreversible effect with reduction in panicle dry weight (Ohe et al., 2007). However, rice genotypes can either escape or avoid high temperatures during anthesis by heading during the cooler periods of the season, by anthesis during cooler hours of early morning, or by increased cooling by transpiration. The heat sensitive physiological processes of anther dehiscence, pollination, pollen germination on the stigma, pollen tube growth or the early events of fertilization can all cause sterility. During the flowering period of 5-7 days, spikelets opening could be affected differently depending on the duration of exposure.

The screening for heat tolerant donors did not reveal any specific subspecies as heat tolerant (Prasad et al., 2006), with an Aus variety N22 showing tolerance to high temperature during anthesis (Jagadish et al., 2008). N22 was also found to be highly drought tolerant with enhanced levels of reactive oxygen scavenging enzymes thus accumulating lower $H_2O_2$ levels under drought.

High temperature during ripening phase in rice primarily affects grain yield and quality; by reduced grain weight, grain size, grain filling, amylose content, and increase in white chalky rice (Osada et al., 1973; Yoshida et al., 1981, Yamakawa et al., 2007; Zhu et al., 2005). These can be caused by excessive energy consumption to meet the respiratory demand of developing seed under high temperature (Tanaka et al., 1995), or higher grain dry matter accumulation rate with a shortened grain-filling period (Kobata and Uemuki, 2004). However, reduction in plant density was shown to increase assimilate production (Kobata and Uemuki, 2004). Cultivar Koshihikari was identified to have increased grain dry matter accumulation during grain-filling and shows reduced percentage of milky white kernels under high temperatures (Kobata and Uemuki, 2004). This points out that an increase in carbohydrate assimilation, either by cultural practice or by genotypic differences can protect against formation of chalky grains and reduction in grain weight.

A rice AP2/ERF class of transcription factor named HYR was overexpressed in rice and was previously shown to improve water use efficiency, photosynthesis, grain yield and drought resistance (Pereira et al. U.S. Patent Publication No. 2014/0223604, which is incorporated herein by reference in its entirety). The HYR protein also was shown to confer resistance to high salinity and low temperature, but no effect of the HYR protein on increasing resistance to high minimal temperatures was previously reported.

In this present invention, the HYR overexpressing rice plants grown under high night/day temperatures showed significantly higher yield under high minimal temperature compared to untransformed control plants. In addition the grain quality, as judged by chalkiness of the grain, showed significantly higher quality with less chalkiness both with respect to the number of grains displaying chalkiness and the level of chalkiness per grain as compared to untransformed control plants. These traits of rice, increased yield and grain quality, in response to high night temperature are of value for rice crop production, and gains more importance with climate change related increases in temperature.

Thus, methods of increasing the resistance of crop plants to heat stress are provided herein. The methods include selecting crop plants for increased expression of the HYR protein of SEQ ID NO: 1, 3, 4, an ortholog thereof, or a sequence with at least 70%, 75%, 80%, 85%, 90%, 92%, 94%, 95%, 96%, 97%, 98%, 99% or more identity to SEQ ID NOs: 1, 3, or 4. SEQ ID NOs: 1, 3, and 4 are the amino acid sequences of three HYR proteins from rice and sorghum. HYR is a transcription factor with homologs or orthologs in diverse species of plants. As used herein homologs refers to two nucleic acid sequences that have the same or similar function, but have evolved separately within a species. As used herein the term ortholog refers to two nucleic acids from different species that share the same or similar functions and have likely evolved from the same ancestral gene via speciation.

In the methods described herein the increased expression of the HYR protein correlates with increased resistance to heat stress in particular to increased minimal or nighttime temperatures, improved grain quality (reduced chalkiness) or improved grain yield of the crop plants on a per plant or per area basis. Increased expression may be measured at either the level of increased HYR mRNA or increased HYR protein expression in cells of the plant, in particular in photosynthesizing cells of the plant. The increased expression is relative to a control plant such as Nipponbare. A control plant is a plant that has not been selected or engineered for resistance to heat stress and in particular for the ability to grow and produce grain in regions with minimal temperatures exceeding 25° C. The expression of HYR protein is generally 2 or more fold higher than the expression of the HYR protein in control plants. Suitably, the expression is increased between 2 and 20 fold, suitably between 2 and 10 fold, or 3 fold, 4 fold, 5 fold, 6 fold, seven fold, eight fold or more as compared to a control plant such as Nipponbare.

Resistance to heat stress indicates that the crop plants demonstrate increased resistance to higher minimal and maximal day/night temperatures and in particular increased minimal temperatures. The resistance to heat stress may be demonstrated by a lack of reduction in the grain yield when the crop plants are grown under conditions of heat stress. Conditions of heat stress may be exemplified by growing the plants under conditions in which the crop plants are exposed to night temperatures of 25° C. or above, suitably 26° C. or above or even 27° C. as the minimal nighttime temperatures. Day temperatures as noted above generally do not have the same negative impact as increased minimal or nighttime temperatures. In particular, the crop plants are most affected by heat stress during the reproductive and ripening phases of growth of the plant. In rice, the increased minimal temperatures and heat stress has the most dramatic impact on grain yield and quality when the plants are exposed to increased temperatures from the boot stage to physiological maturity.

The grain yield may be measured by total yield/area or yield per plant. As demonstrated in the examples, the grain yield per plant in plants with increased expression of HYR protein may be over 5 g/plant when grown under conditions of heat stress as compared to less than 4 g/plant in controls. Suitably, the grain yield is over 5 g/plant, over 6 g/plant, over 7 g/plant or even more depending on the level of heat stress, timing of stress and length of exposure. The resistance to heat stress may also be demonstrated by maintenance of grain quality after exposure to heat stress as defined herein. The grain may be small in size or demonstrate an increase in chalkiness of the grains after exposure to heat. Overexpression of HYR protein may protect the crop plants from the reductions in grain quality. As shown in the examples, the grains were less likely to be chalky and those that were chalky were less chalky than grain from control plants not overexpressing HYR protein. In the examples, the rice was 15-20% less chalky in the HYR transgenic plants as compared to the wild-type plants when grown under heat stress. Suitably, the grain quality is improved by a 7, %, 8%, 9%, 10% 11%, 12%, 14%, 15%, 16%, 18%, or even 20% reduction in chalkiness of the grain from plants when grown under heat stress. The reduction in chalkiness of the grains will depend on the level of heat stress, duration and timing of the exposure to such stress.

Methods of using an HYR protein are also provided. The methods include generating a transgenic plant engineered to overexpress the HYR protein of SEQ ID NO: 1, SEQ ID NO: 3, SEQ ID NO: 4, or an ortholog of these sequences with at least 80% amino acid identity to at least one of SEQ ID NO: 1, 3 or 4. The transgenic plants include the HYR protein operably connected to a promoter or transcription regulatory sequence active in plant cells and capable of increasing the expression of the HYR protein as compared to the expression of the native protein in the plant cells. The transgenic plants are then grown in conditions or regions expected to experience heat stress or minimal nighttime temperatures in excess of 25° C., suitably 26° C. or above for at least a portion of the growing season. The transgenic plants will be expect to offer better yields of grain in areas experiencing heat stress as compared to control non-transgenic plants.

The HYR gene expressing rice lines in the Examples have an alteration in gene and protein expression that is involved in the plant phenotypes of temperature tolerance and grain quality. Some of the genes whose expression is controlled by the HYR protein transcription factor are therefore responsible for these improved traits. It is expected that some of these genes are also responsible for the trait of high temperature tolerance in some varieties and cultivars that have different alleles. Identification of the genes regulated by HYR and conferring heat tolerance will provide molecular markers for improving rice and other crop plants for high temperature tolerance and grain quality.

Thus, methods of screening for crop plant proteins capable of increasing resistance of crop plants to heat stress are provided herein. First the sequences whose expression is increased or decreased in response to expression of a HYR protein are identified. The HYR protein has a polypeptide sequence selected from those of SEQ ID NO: 1, SEQ ID NO: 3, SEQ ID NO: 4, or an ortholog of these sequences or a sequence with at least 80% identity to at least one of SEQ ID NOs: 1, 3, or 4. Then the sequences are analyzed to determine if they are required for resistance to heat stress in a plant cell or transgenic plant. Those sequences that are required for resistance to heat stress may be useful targets for generation of plants with increased resistance to heat stress.

The expression of the sequences may be evaluated using any means available to those of skill in the art including but not limited to microarray analysis, rtPCR, real-time quantitative rtPCR, Northern blot analysis, RNA-sequencing, Western blot analysis, or any other means of evaluating the expression of the sequences at either the RNA or protein expression level. The key sequences involved in mediating the resistance to heat stress in the crop plants may then be identified by comparing the expression of the sequences in response to overexpression of the HYR protein to the expression of the sequences when HYR is not expressed or not overexpressed by the plant cells.

Those sequences whose expression is affected by the change in expression of HYR protein are candidate sequences for mediating the resistance to heat stress. These candidate sequences can then be analyzed for their individual or group ability to increase resistance of crop plants to heat stress. Those of skill in the art will appreciate that this step may be carried out in plant cells or in transgenic plants in which the expression of the affected sequence(s) can be manipulated to investigate the ability of the sequence(s) to alter at least one phenotype related to resistance to heat stress in the crop plant or in crop plant cells.

The expression of the affected sequences may be altered in plants, plant parts or plant cells using a variety of techniques available to those skilled in the art including but not limited to transgenic, or other recombinant technologies to mediate over-expression of sequences or knock-out or knock-down (i.e. miRNA methodologies) to test the results of decreased expression. The changed expression of these affected sequences may then be assessed for their effect on one or more phenotype associated with heat stress including but not limited to an increase in at least one of biomass, chloroplasts, photosynthesis, roots, response to light intensity, or increased seed weight, increased grain yield, or lack of chalkiness, after exposure to increased temperatures in a cell incapable of increasing HYR expression.

Methods of producing grain in regions having minimal temperatures at or above 25° C. are also provided. Crop plants having at least two fold or more increased expression of the HYR protein as described above in relation to a control plant are selected and planted in a region expected to or at risk of having minimal temperatures at or above 25° C. during the growing season. The method ensures good crop yields in areas at risk of having temperatures likely to reduce the grain yield. The plants may have increased expression by being transgenic for the HYR protein or may be generated through traditional breeding such as a hybrid. The minimal temperatures during the growth season may be experienced from the boot stage through physiological maturity or for only a portion of this time. The temperatures may be at or above 26° C. for minimal temperatures.

The HYR sequences disclosed herein are from a plant, including but not limited to a rice plant, a sorghum plants, an *Arabidopsis* plant, a canola plant, a soybean plant, a barley plant, a sunflower plant, a linseed plant, a wheat plant, or a maize plant. The crop plant thus may be selected from at least one of *Zea, Oryza, Triticum, Solanum, Hordeum, Brassica, Glycine, Phaseolus, Avena, Sorghum, Saccharum, Gossypium, Populus, Quercus, Salix, Miscanthus* and *Panicum*.

A plant includes any portion of the plant including but not limited to a whole, plant, a portion of a plant such as a root, leaf, stem, seed, pod, flower, cell, tissue or plant germplasm or any progeny thereof. Plants also include transgenic plants and non-genetically modified plants. Germplasm refers to genetic material from an individual or group of individuals or a clone derived from a line, cultivar, variety or culture. Rice plant refers to whole rice plant or portions thereof including, but not limited to, plant cells, plant protoplasts, plant seeds, plant tissue culture cells or calli. A plant cell refers to cells harvested or derived from any portion of the plant or plant tissue culture cells or calli. Plant parts, include but are not limited to stems, roots, ovules, stamens, leaves, embryos, meristematic regions, callus tissue, gametophytes, sporophytes, pollen, microspores, and the like.

A polynucleotide encoding the HYR protein may be transformed into and expressed in plant cells using conventional recombinant technologies such as those described in International Patent Application WO2012/158594. The nucleic acid may be operably linked to a promoter functional in plant cells. The promoter may be a constitutive promoter, an inducible promoter a tissue-specific promoter or a developmentally regulated promoter. In the examples, the CaMV35S constitutive promoter was used to drive expression of HYR.

The expression of the HYR protein may be increased by a number of methods available to those of skill in the art. For example the expression may be increased using recombinant DNA technology, e.g., by using a strong promoters to drive increased expression of a polynucleotide encoding the HYR protein. Alternatively the copy number of the polynucleotide encoding the HYR protein may be increased in the plant, in cells of the plant. Alternatively, the expression of the HYR protein could be increased by identifying plants in which the HYR protein is already expressed at a higher level. These plants may then be used in traditional breeding, such as by generation of hybrids having increased expression of the HYR protein. Other mechanisms for increasing the expression of HYR protein include, but are not limited to, increasing expression of a transcriptional activator, reducing expression of a transcriptional repressor, addition of an enhancer region capable of increasing expression of HYR protein, increasing mRNA stability, altering DNA methylation, histone acetylation or other epigenetic or chromatin modifications in the vicinity of the relevant genes, or increasing protein or polypeptide stability.

Non-transgenic means of generating plant varieties carrying traits of interest such as increased resistance to heat stress via increased expression of HYR protein are available to those of skill in the art and include traditional breeding, chemical or other means of generating chromosome abnormalities, such as chemically induced chromosome doubling and artificial rescue of polyploids followed by chromosome loss, knocking-out DNA repair mechanisms or increasing the likelihood of recombination or gene duplication by generation of chromosomal breaks. Other means of non-transgenically increasing the expression or copy number of HYR polynucleotide or protein include the following: screening for mutations in plant DNA encoding miRNAs or other small RNAs, or other genetic elements that impact HYR expression; screening large field or breeding populations for spontaneous variation in copy number or sequence at the HYR gene by screening of plants for resistance to heat stress, copy number or other gene or protein expression traits as described above; crossing of lines that contain different or the same HYR genes but have distinct polymorphisms on either side, followed by selection of recombinants using molecular markers from the two distinct genotypes flanking the HYR gene; chemical or radiation mutagenesis or plant tissue culture/regeneration that creates chromosome instability or gene expression changes, followed by screening of plants for resistance to heat stress; or introduction by conventional genetic crossing of non-transgenic loci that create or increase genome instability, followed by screening of plants for either heat stress resistance. Examples of loci that could be used to create genomic instability include active transposons (natural or artificially introduced from other species), loci that activate endogenous transposons (for example mutations affecting DNA methylation or small RNA processing such as equivalent mutations to met1 in *Arabidopsis* or mop1 in maize), mutation of plant genes that impact DNA repair or suppress illegitimate recombination such as those orthologous or similar in function to the Sgs1 helicase of yeast or RecQ of *E. coli*, or overexpression of genes such as RAD50 or RAD52 of yeast that mediate illegitimate recombination. Those of skill in the art may find other transgenic and non-transgenic methods of increasing expression of the HYR protein through transgenic or non-transgenic means.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements. The terms "a", "an" and "the" may mean one or more than one unless specifically delineated.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

The following examples are meant only to be illustrative and are not meant as limitations on the scope of the invention or of the appended claims. All references, included patents, patent publications and non-patent literature, cited herein are hereby incorporated by reference in their entirety. Any conflict between statements in references and those made herein should be resolved in favor of the statements contained herein.

Examples

Rice genotypes overexpressing the HYR gene under control of the CaMV35S promoter were compared to non-transformed Nipponbare control plants in replicated experiments grown in the greenhouse and tested in growth chambers for their response to temperature stress. See International Publication No. WO2012/158594 for a description of the development of the HYR transgenic plants. Notably, these plants were described therein as having increased drought resistance, resistance to salinity and low temperature stress. Resistance to increased minimal temperatures was not known. The day/night cycle of photoperiod was 14 h/10 h in both growth chamber and the greenhouse.

For high temperature stress during vegetative stage, a set of 50-day-old HYR lines and Nipponbare control plants were moved into controlled environment growth chambers (Conviron Model PGW36) set at day/night temperature of 34/24° C. for 10 days. The light intensity measured at 60 cm above the canopy was 600 μmol/m2/s and the relative humidity was 70%. During the reproductive stage, plants at early boot stage were exposed to high day/night temperature stress of 36/26° C. for 20 days.

For non-stress conditions at both vegetative and reproductive stage, another set of HYR lines and Nipponbare control plants were maintained in the greenhouse with day/night temperature of 26/22° C. The light intensity measured in the greenhouse was 800 μmol/m2/s with relative humidity of 70%.

Analysis of the replicated trial of two independent HYR lines under high temperature treatment showed that HYR lines had significant increase of ~50% in total grain yield (FIG. 1A) compared to the untransformed wild-type Nipponbare. The yield components spikelet fertility and 100 seed weight, were however not consistently higher in the HYR lines compared to wild-type under high temperature (FIG. 1B/C).

Figure 2:
FIG. 2 is a set of photographs showing the high nighttime temperature effect on rice Nipponbare wild-type and HYR lines. The photos show the effect of high nighttime temperature from boot stage to maturity. The wild-type show chalkiness, which is reduced in the HYR overexpression lines by about 15-20%.

Further analysis of the grain quality as judged for chalkiness (FIG. 2) showed that the HYR lines under temperature stress showed a lower number of chalky grains and a lower percentage of chalkiness of the grains. Thus both grain yield and grain quality were improved in the HYR lines as compared to the control lines after exposure to heat stress.

REFERENCES

Baker J T, Allen Jr. L H, Boote K J (1992) Temperature effects on rice at elevated CO2 concentration. J Exp Bot. 43: 959-964.

Imin N, Kerim T, Rolfe B G, Weinman J J (2004). Effect of early cold stress on the maturation of rice anthers. Proteomics 4, 1873-1882.

Jagadish S V K, Craufurd P Q, Wheeler T R (2008) Phenotyping parents of mapping populations of rice (*Oryza sativa* L.) for heat tolerance during anthesis. Crop Sci. 48, 1140-1146.

Kobata T, Uemuki N (2004) High temperatures during the grain-filling period do not reduce the potential grain dry matter increase of rice. Agron. J. 96, 406-414.

Matsui T, Omasa K, Horie T (2000) High temperature at flowering inhibit swelling of pollen grains, a driving force for thecae dehiscence in rice (*Oryza sativa* L.). Plant Prod. Sci. 3: 430-434.

Oh-e I, Saitoh K, Kuroda T (2007) Effects of high temperature on growth, yield and dry-matter production of rice grown in the paddy field. Plant Prod. Sci. 10, 412-422.

Osada A, Sasiprada V, Rahong M, Dhammanuvong S, Chakrabandhu M (1973) Abnormal occurrence of empty grains of indica rice plants in the dry, hot season in Thailand. Proc. Crop Sci. Soc. Jpn. 42, 103-109.

Pereira A, Ambavaram M M R, Batlang U (2012) Crop plants with improved water use efficiency and grain yield and methods of making them. WO 2012/158594 A2, 22 Nov. 2012

Peng S B, Huang J L, Sheehy J E, Laza R C, Visperas R M, Zhong X H, Centeno G S, Khush G S, Cassman K G (2004) Rice yields decline with higher night temperature from global warming. Proc. Natl. Acad. Sci. USA. 101: 9971-9975.

Prasad P V V, Boote K J, Allen L H, Sheehy J E, Thomas J M G (2006) Species, ecotype and cultivar differences in spikelet fertility and harvest index of rice in response to high temperature stress. Field Crops Research 95: 398-411.

Qin F, Shinozaki K, Yamaguchi-Shinozaki K (2011) Achievements and challenges in understanding plant abiotic stress responses and tolerance. Plant Cell Physiol. 52:1569-82.

Savchenko G E, Klyuchareva E A, Abrabchik L M, Serdyuchenko E V (2002) Effect of periodic heat shock on the membrane system of etioplasts. Russ. J. Plant Physiol. 49: 349-359.

Sheoran I S, Saini H S (1996) Drought-induced male sterility in rice: Changes in carbohydrate levels and enzyme activities associated with the inhibition of starch accumulation in pollen. Sexual Plant Reprod. 9, 161-169.

Tanaka K, Kasai Z, Ogawa M (1995) Physiology of ripening. In "Science of the Rice Plant. Vol. 2. Physiology" (T. Matsuo, K. Kumazawa, K. I. Ishii, and H. Hirata, Eds.), pp. 07-118. Food and Agriculture Policy Research Center, Tokyo.

Tripathy J N, Zhang J, Robin S, Nguyen T T, Nguyen, H T (2000) QTLs for cell-membrane stability mapped in rice (*Oryza sativa* l.) under drought stress. Theor. Appl. Genet. 100, 1197-1202.

Wahid A, Gelani S, Ashraf M, Foolad M R (2007) Heat tolerance in plants: An overview. Environ. Exp. Bot. 61, 199-223.

Wassmann R, S. V. K. Jagadish S V K, Heuer S, Ismail A, Redona E, Serraj R, Singh R K, Howell G, Pathak H, Sumfleth K (2009) Climate change affecting rice production: The physiological and agronomic basis for possible adaptation strategies. Adv Agron 101: 59-122.

Welch J R, Vincent J R, Auffhammer M, Moya P F, Dobermann A, Dawe D (2010) Rice yields in tropical/subtropical Asia exhibit large but opposing sensitivities to minimum and maximum temperatures. Proc Natl Acad Sci USA. 107(33): 14562-7.

Yamakawa H, Hirose T, Kuroda M, Yamaguchi T (2007) Comprehensive expression profiling of rice grain filling-related genes under high temperature using DNA microarray. Plant Physiol. 144: 258-277.

Yoshida S, Satake T, Mackill D (1981) High temperature Stress. IRRI Res. Pap. 67, 1-15.

Zhu C, Xiao Y, Wang C, Jiang L, Zhai H, Wan J (2005) Mapping QTL for heat-tolerance at grain filling stage in rice. Rice Sci. 12, 33-38.

We claim:

1. A method of producing grain in regions having minimal temperatures of 25° C. or above comprising generating a transgenic rice crop plant comprising a polynucleotide encoding a HYR protein operably connected to a promoter functional in cells of the plant, wherein the plant has at least two fold higher expression of the HYR protein as compared to a control plant, and wherein the HYR protein comprises SEQ ID NO: 1 or a sequence with at least 95% identity to SEQ ID NO: 1; and planting the transgenic rice crop plant in a region expected or at risk of having minimal temperatures of 25° C. or above during the growing season of the plant.

2. The method of claim 1, wherein the region is at risk of having minimal temperatures at or above 26° C. during the growth season from boot stage through physiological maturity.

3. The method of claim 1, wherein the control plant is Nipponbare.

4. The method of claim 1, wherein the HYR protein comprises SEQ ID NO: 1.

5. The method of claim 1, wherein the minimal temperature is 26° C. or above.

6. The method of claim 1, wherein the minimal temperatures of 25° C. or above are experienced from the boot stage through physiological maturity.

7. The method of claim 1, wherein the grain yield per plant is at least 5 g/plant when the minimal temperatures are 25° C. or above.

8. The method of claim 1, wherein the grain quality produced by the transgenic rice crop plant shows at least a 7% reduction in chalkiness as compared to the control plant.

9. The method of claim 1, wherein the expression of the HYR protein is increased at least 4 fold as compared to the control plant.

10. The method of claim 1, wherein the expression of the HYR protein is increased at least 5 fold as compared to the control plant.

* * * * *